United States Patent [19]
Cheburkov

[11] Patent Number: 5,466,879
[45] Date of Patent: Nov. 14, 1995

[54] PRODUCTION OF HEXAFLUOROACETONE AND ITS OXIME

[75] Inventor: Yuri Cheburkov, Woodbury, Minn.

[73] Assignee: Minnesota Mining and Manufacturing Company, St. Paul, Minn.

[21] Appl. No.: 341,838

[22] Filed: Nov. 18, 1994

Related U.S. Application Data

[63] Continuation-in-part of Ser. No. 202,999, Feb. 28, 1994, abandoned.

[51] Int. Cl.$^6$ .................................................. C07C 249/06
[52] U.S. Cl. .................................. 564/253; 568/404
[58] Field of Search ..................... 568/404, 411, 568/419; 564/253, 263

[56] References Cited

U.S. PATENT DOCUMENTS

| | | | |
|---|---|---|---|
| 3,213,134 | 10/1965 | Morin | 568/386 |
| 3,321,515 | 5/1967 | Moore et al. | 568/386 |
| 4,337,361 | 6/1982 | Anello et al. | 568/386 |
| 4,357,282 | 11/1982 | Anderson et al. | 568/383 |
| 4,960,947 | 10/1990 | Sonoi et al. | 568/399 |

FOREIGN PATENT DOCUMENTS 53073504  6/1978  Japan.

OTHER PUBLICATIONS

Cheburkov et al., Vysokomol. Soedin, Ser. B., Vol. 9, p. 181 (1967).
Cheburkov et al, Izv. Akad Nauk SSSR, Ser. Khim., #4, pp. 829–833 (1967) (English).
Cheburkov, Yuri, et al., "Oxime Hexafluoroactetone as a Solvent," Vysokomol. Soedin., Ser. B, 9(3), 181 (1967).
L.G. Anello, "Journal of Organic Chemistry", 47, p. 377, 1982.
Y. A. Cheburkov et al., Izv. Akad. Nauk SSSR, Ser. Khim., No. 2, pp. 367–369, 1964 (English).
Y. A. Cheburkov et al., Izv. Akad. Nauk SSSR, Ser. Khimi., No. 6, pp. 1395–1396, 1967 (English).
Y. Cheburkov et al., Izv. Akad. Nauk SSSR, Ser. Khimi., No. 12, pp. 2119–2122, 1966 (English).
Chem Abs., vol. 55, p. 4364, (1961).
Chem. Abs., vol. 57, p. 12327e, (1962).
Chem. Abs., vol. 62, p. 6397a, (1964).
Chem. Abs., vol. 67, 11837n, (1967).
Chem. Abs. vol. 67, 53644, (1967).
Chem. Abs., vol. 68, 2586(y), p. 2589, (1966).
Chem. Abs., vol. 62, 1570g, (1965).
Chem. Abs., vol. 58, 8914b, (1963).
England et al., "Journal of Fluorine Chemistry", vol. 3, pp. 63–70, 1973/74.
Y. Inouye et al., "Journal of Fluorine Chemistry", 27, p. 379, 1985.
I. L. Knunyants et al., Izv. Adad. Nauk SSSR, Ser. Khim., No. 1, pp. 54–60, 1972 (English).
I. L. Knunyants et al., Izv. Adad. Nauk SSSR, Ser. Khim., No. 8, pp. 1393–1397, 1963 (English).
Edited by: I. L. Knunyants et al., "Syntheses of Fluoroorganic Compounds", Springer–Verlag, Berlin, pp. 40–54, 1985.
I. L. Knunyants et al., Zhurnal Vses. Khim. Ob–va Im. Mendeleeva, vol. 15, pp. 17–30, 1970 (English).
S. T. Kocharyan et al., Izv. Akad. Nauk SSSR, Ser. Khim., No. 4, pp. 846–854, 1968 (English).
C. G. Krespan, "Journal of Organic Chemistry", vol. 34, No. 5, pp. 1278–1280, 1969.
V. F. Snegirev et al., "Journal of Fluorine Chemistry", 17, pp. 441–445, 1981.
T. A. Treat; "U.S. Defensive Publication"; T983,009; 1979.
M. V. Urushadze, Izv. Akad. Nauk SSSR, Ser. Khimi., No. 5, pp. 1137–1145, 1972 (English).
M. V. Urushadze et al., Izv. Akad. Nauk SSSR, Ser. Khimi., No. 6, pp. 1347–1353, 1972 (English).
S. T. Kocharyan et al., Izv. Akad. Nauk SSSR, Ser. Khim., No. 6, p. 1397, 1967 (English).
Koshar et al., "Journal of American Chemical Society", 79, pp. 1741–1744, 1957.
A. Morse et al., Canadian Journal of Chemistry, 33, p. 453 (1955).

*Primary Examiner*—James H. Reamer
*Attorney, Agent, or Firm*—Gary L. Griswold; Walter N. Kirn; Eloise J. Maki

[57] ABSTRACT

A method of making hexafluoroacetone from hexafluoroacetone oxime comprising heating hexafluoroacetone oxime (or solvent complex thereof) with a concentrated mineral acid to yield hexafluoroacetone. Also a method of making hexafluoroacetone oxime from hexafluoroisobutyroyl carbanion alkylammonium salts. The oxime can be prepared by reacting the salts in solvent with an alkali or alkaline earth metal nitrite and subsequently decarboxylating and hydrolyzing the reaction product, or alternatively, reacting the salts in a solvent with dinitrogen tri- or tetra-oxide and subsequently decarboxylating and hydrolyzing the reaction product.

16 Claims, No Drawings

PRODUCTION OF HEXAFLUOROACETONE AND ITS OXIME

This is a continuation-in-part of application Ser. No. 08/202,999 filed Feb. 28, 1994, now abandoned.

This invention relates to the production of hexafluoroacetone. In another aspect, it relates to the production of hexafluoroacetone oxime. In another aspect, it relates to the production of useful products from the adducts of alcohol and perfluoroisobutene, a highly toxic by-product in the manufacture of hexafluoropropene.

Hexafluoroacetone, $(CF_3)_2CO$, is an important industrial fluorochemical that is useful, for example, as an intermediate for crosslinking agents used in the manufacture of fluoroelastomer polymer fabricated into thermally-stable hoses, etc., necessary to meet the severe operating conditions of modern automobile engines. Various processes have been used or proposed for the preparation of hexafluoroacetone (or its hydrate), many of which are described in U.S. Pat. No. 4,960,947 (Sonoi et al.), including certain processes for thermally decomposing alcohol adducts of perfluoroisobutene, a highly toxic by-product produced as a waste stream in the manufacture of hexafluoropropene.

Hexafluoroacetone oxime is useful as a solvent for polyamide, polyester, and polyether polymers. For instance, nylon is soluble up to 20 weight % in hexafluoroacetone oxime at room temperature (see Yu. A. Cheburkov et al., Vysokomol. Soedin., Ser. B, 9(3), 190–192 (1967)).

In one aspect, this invention provides a process for the production of hexafluoroacetone, comprising heating, for example, by refluxing, hexafluoroacetone oxime, $(CF_3)_2C=NOH$, (or a solvent complex thereof) with a concentrated mineral acid, such as those acid solutions having a concentration of 85 to 99%, e.g., sulfuric acid or phosphoric acid, to hydrolyze the oxime. Such heating can be carried out in a vessel or reactor provided with a reflux condenser, e.g., at 100° to 150° C., for a sufficient time to hydrolyze the oxime. The following scheme illustrates this hydrolysis.

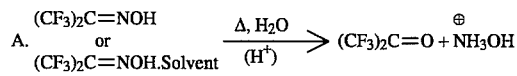

In the above scheme, $(CF_3)_2C=NOH.Solvent$ represents a complex of hexafluoroacetone oxime with a basic organic solvent having oxygen and/or nitrogen atoms, such as acetonitrile, $CH_3CN$, or an organic or alkanoic acid solvent, such as acetic acid, $CH_3COOH$.

The resulting gaseous hexafluoroacetone product of the hydrolysis reaction can be condensed and collected, for example, in a cold acetone-dry ice trap at −78° C. The condensed hexafluoroacetone gas (with a high purity, e.g., 97% or higher, as determined by gas chromatographic analysis) can be purified further and isolated, for example, by evaporation of the condensed gas and recondensing it by passing it into a water trap or in glass tube for storage. In the water trap, the hexafluoroacetone is converted into its hydrate, which can be so-obtained with high purity, e.g., 99% or higher, as determined by nuclear magnetic resonance analysis. A residue may be left in the acetone-dry ice trap after the hexafluoroacetone evaporation and usually will comprise hexafluoroacetone hydrate (e.g., about 30%), hexafluoroacetone oxime (e.g., about 60%), and impurities (e.g., about 10%); the residue can be recycled to the reactor.

The above-described process can be used to produce the hexafluoroacetone in high yield, e.g., 85% or higher, based on the hexafluoroacetone oxime starting material, if the mineral acid used is highly concentrated, e.g., 96% concentrated sulfuric acid. A somewhat lower yield, e.g., 30–85%, may result if the concentration of the acid used is relatively lower, e.g., 85% concentrated sulfuric acid, and such less concentrated acid may require that the reaction or hydrolysis be extended or relatively longer in order to obtain the high yield.

As mentioned above, the hexafluoroacetone oxime starting material may be used in the form of a solvent complex thereof. Such complexes are known—see, for example, Cheburkov et al., ibid., which describes the formation of stable 1:1 molar complexes of hexafluoroacetone oxime with acetonitrile, dimethylformamide, dioxane, etc., which description is incorporated herein. If desired, the free oxime may be first regenerated from the complex by distillation at reduced pressure and lower temperature from a mixture of the complex with concentrated sulfuric acid (but with no hydrolysis to the free hexafluoroacetone). In the special case of a solvent complex of hexafluoroacetone oxime with dimethylformamide (DMF), it is necessary to so-regenerate the free oxime and use it as the starting material since gaseous carbon monoxide may be otherwise formed during the DMF hydrolysis with sulfuric acid, and the carbon monoxide is likely to prevent efficient trapping of the gaseous hexafluoroacetone product. Generally, the other solvents which can be complexed with the hexafluoroacetone oxime, include for example, basic oxygen- and/or nitrogen-containing organic solvents such as nitriles, e.g. acetonitrile, tertiary amines, e.g. trialkyl amines containing methyl or ethyl groups, dialkylamides, e.g. dimethylformamide and dimethylacetamide, ketones, e.g. acetone or methyl ethyl ketone, simple ethers, e.g. diethyl ether or tertiary butyl methyl ether, alcohols, e.g. lower alkanols, and esters, e.g. acetates. and also aliphatic organic acids containing from 1 to 4 nonhalogenated carbon atoms the skeletal chain of which optionally includes one or more caternary heteroatoms such as divalent oxygen or trivalent nitrogen and which will be stable under the hydrolysis reaction conditions and for which the hexafluoroacetone oxime need not be regenerated from the complexes before hydrolysis e.g., acetic, propionic, or butyric acid.

Generally, in carrying out the hydrolysis of the hexafluoroacetone oxime (or its solvent complex) according to this invention, no significant, if any, waste gases or solids are produced, other than an acid solution of hydroxylamine by-product, $NH_2OH$ (and organic solvent in the case where an oxime solvent complex is used as starting material).

The hexafluoroacetone oxime or its solvent complex, used as starting material in the practice of this invention, can be prepared by many known processes. For example, hexafluoroacetone oxime can be derived from perfluoroisobutene (see Yu. A. Cheburkov et al.; *Izvestiya Akademii Nauk SSSR, Seriya Khimicheskaya*, No. 4, pp. 829–833 (1967)) or its derivatives (see Yu. A. Cheburkov et al., ibid., No. 12, pp. 2119–2122 (1966); U.S.S.R. Pat. 187,027, *Chem. Abs.* Vol. 67, P53644c (1967)); and see the processes of making the oxime that are described (with citations) in "Synthesis of Fluoroorganic Compounds," edited by I. L. Knunyants et al., Springer-Verlag, Berlin, Heidelberg, New York, Tokyo, p. 49 (1985).

Another process (believed novel) for preparation of the hexafluoroacetone oxime, useful as a starting material in preparing hexafluoroacetone according to this invention, is a process which utilizes the mesomeric hexafluoroisobutyroyl carbanion alkylammonium salts. Such salts can be formed by reacting a tertiary amine, such as a trialkylamine wherein each of the three constituent groups contains from 1 to 3 straight chained carbon atoms, preferably with only one such group containing 3 carbon atoms, e.g., trimethylamine or triethylamine, or pyridine, with 2H-hexafluoroisobutyryl fluoride, $(CF_3)_2CHCOF$, or with the unsaturated adducts of perfluoroisobutene with an alcohol, such as a lower alkanol, e.g., methanol, ethanol, propanol, butanol, and isopropanol. Perfluoroisobutene is a highly toxic fluorocarbon produced as a by-product wastestream in the manufacture of hexafluoropropene. The preparation of such salts are described by I. L. Knunyants et al., *Zhurnal Vses. Khim. Obshchestva im. Mendeleeva*, Vol. 15, pp. 17–30 (English) (1970); Yu. A. Cheburkov et al., *Izv. Akad. Nauk SSSR, Ser. Khim.* No. 2, pp. 367–369 (1964) and No. 6, pp. 1395–1396 (1967); I. L. Knunyants et al.,*Izv. Akad. Nauk SSSR Ser. khim.* No. 8, pp. 1393–1397 (1963) and No. 1, pp. 54–60 (1972); S. T. Kocharyan et al., *Izv. Akad Nauk SSSR, Ser. Khim.*, No. 6, p. 1397 (1967) and No. 4, pp. 846–854 (1968); M. V. Urushadze et al., No. 5, pp. 1137–1145 (1972); and Y. Inouye et al., *Jour. Fluorine Chemistry*, 27, 379 (1985), which descriptions are incorporated herein. Schemes for the preparation such salts from the principal methanol adduct of perfluoroisobutene are as follows:

B. $(CF_3)_2CHCF_2OCH_3 \xrightarrow[-N(C_2H_5)_3 \cdot HF]{N(C_2H_5)_3}$ $(CF_3)_2C=CFOCH_3 \xrightarrow{N(C_2H_5)_3}$ $(CF_3)_2C-CF-O\;(C_2H_5)_3NCH_3$ with $\overset{\ominus}{+506}\;\oplus$ In accordance with such other aspects of this invention, to prepare hexafluoroacetone oxime the intermediate perfluoroalkenolate quaternary ammonium salts are (i) reacted in a solvent with alkali or alkaline earth metal nitrite, $M^v{}_{1/v}NO_2$ (where "V" is the valence of the metal "M"), e.g., sodium nitrite, followed by decarboxylation and hydrolysis, or are (ii) reacted in a solvent with dinitrogen tri- or tetra-oxide, followed by decarboxylation and hydrolysis. Useful solvents for this purpose are the aforementioned basic oxygen- and/or nitrogen-containing solvents used to make the hexafluoroacetone oxime solvent complexes. Schemes for the production of hexafluoroacetone oxime by these novel processes are as follows:

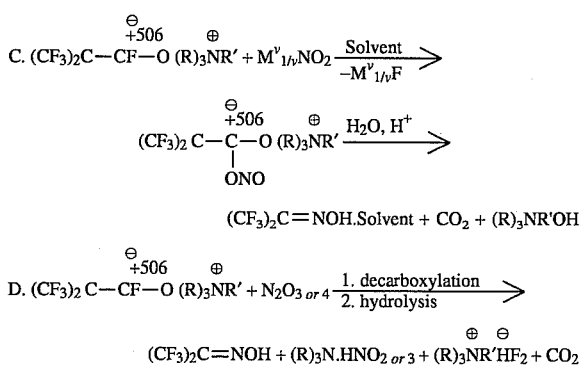

C. $(CF_3)_2C-CF-O\;(R)_3NR' + M^v{}_{1/v}NO_2 \xrightarrow[-M^v{}_{1/v}F]{\text{Solvent}}$ $(CF_3)_2C-\underset{\underset{ONO}{|}}{C}-O\;(R)_3NR' \xrightarrow{H_2O,\;H^+}$ $(CF_3)_2C=NOH.\text{Solvent} + CO_2 + (R)_3NR'OH$ D. $(CF_3)_2C-CF-O\;(R)_3NR' + N_2O_{3\;or\;4} \xrightarrow[\text{2. hydrolysis}]{\text{1. decarboxylation}}$ $(CF_3)_2C=NOH + (R)_3N.HNO_{2\;or\;3} + (R)_3NR'HF_2 + CO_2$ The reactions of the above schemes B, C, or D can be carried out in sequence in one reactor (or "pot") to prepare hexafluoroacetone oxime without isolation and recovery of the intermediates (i.e., the products of reaction schemes B, C, and D), as illustrated by the following overall scheme, E.

E. $(CF_3)_2CHCF_2OR' + 2(R)_3N + N_2O_{3\;or\;4} \xrightarrow[\text{Solvent}]{H_2O}$ $(CF_3)_2C=NOH.\text{Solvent} +$ $(R)_3N.HNO_{2\;or\;3} + (R)_3NR'HF_2 + CO_2 \uparrow$ To recover the hexafluoroacetone oxime from the reaction product mixture of Schemes C, D, and E, such mixture can be washed with water to remove the ammonium salts and solvent and the washed residue can be treated with concentrated mineral acid such as 96% sulfuric acid to liberate the oxime from its solvent complex and to dry the oxime. The oxime can be distilled from the acid mixture.

Objects and advantages of this invention are illustrated in the following examples.

EXAMPLE 1

Hexafluoroacetone (HFA) from hydrolysis of HFA oxime.

In a system comprising a three-neck flask equipped with magnetic stirrer, dropping funnel, gas-inlet tube, and a Dewar condenser cooled to 0° C. and connected with a trap (−78° C.) by Kel-F™ rubber tubing, and two bubblers with concentrated sulfuric acid at both ends of the system, were placed 4 ml of concentrated (96%) sulfuric acid and the system was allowed to dry for an hour in a flow of dry nitrogen. Hexafluoroacetone oxime (1.84 g of 95% purity according to gas chromatography, "GC", analysis) was added and the resulting two-layer mixture was refluxed for 2 hours with vigorous stirring until the upper oxime layer completely disappeared. Dry nitrogen was used to purge the reaction product through the system. There was collected in the trap 1.54 g of crude condensed hexafluoroacetone, which was then evaporated and recondensed (1.25 g) into a water trap. A gaseous sample of hexafluoroacetone ("HFA") was withdrawn directly from the exit gas stream for GC analysis. Such analysis showed the sample consisted of 97.1% HFA, 0.7% HFA hydrate, 0.5% HFA oxime and 1.7% unknown low boilers (also present in the starting oxime). Fluorine-19 nuclear magnetic resonance, "$^{19}$F-NMR", analysis of HFA hydrate obtained in the water trap was used to quantify the relative concentrations of the major components and a couple of the minor components. The results were the following: HFA hydrate, 99.7%; HFA oxime, 0.2%; unknown, $CF_3CR_2R_2$, 0.1%. The residue (0.29 g) in the trap after HFA evaporation was found by GC analysis to comprise 62% HFA oxime (0.18 g) and 26% HFA hydrate (0.07 g). Yield of HFA based on raw material was calculated as follows:

$$\frac{1.25 \times 100 \times 181}{1.84 \times 0.95 \times 166} = 78\%$$

Yield of HFA based on the oxime conversion:

$$\frac{(1.25 + 0.07) \times 100 \times 181}{(1.84 \times 0.95 - 0.18) \times 166} = 92\%$$

EXAMPLE 2

HFA from hydrolysis of HFA oxime.

In this Example, the same procedure was used as in Example 1 except 1.81 g of HFA oxime with 95% content and 3.2 g of 85% sulfuric acid were used in the reaction. After refluxing for 6 hours, 0.91 g of crude HFA gas was collected in a trap (−78° C.). After 0.6 g HFA was evaporated and recondensed, there was left 0.31 g residue which comprised 62% HFA oxime and 30% HFA hydrate. Yield of HFA based on HFA oxime was 38%. Yield of HFA based on the oxime conversion was 67%.

EXAMPLE 3

HFA from hydrolysis of HFA oxime solvent complexes.

In this Example, a number of runs were carried out with different hexafluoroacetone oxime.solvent complexes. In each run the same procedure as in Example 1 was followed except 1.81 g of HFA oxime (95% purity) was mixed with equimolar quantity of a solvent prior to reflux with 10 ml of concentrated sulfuric acid. The HFA gas was condensed and collected in a trap (−78° C.) and recondensed in glass tube for storage. The results are shown in the Table I.

of concentrated sulfuric acid. The results are shown in the following Table 2.

EXAMPLE 5

HFA from reaction of 1-methoxy-2H-octafluoroisobutane with nitrogen dioxide.

To 3.48 g (0.015M) of 1-methoxy-2H-octafluoroisobutane in 6 ml of dry acetone, 2.52 g (0.025M) of triethylamine was added at 0° C. with stirring and the mixture was allowed to warm to room temperature for 1 hour. Nitrogen dioxide (1.38 g, 0.016M) was condensed into the mixture at −10° C. Slow evolution of carbon dioxide began at −8° C. and finished at 10° C. The mixture was then allowed to stand at room temperature for 3 hours and then 7 ml of 15% hydrochloric acid was added. The resulting lower organic layer containing HFA oxime (as determined GC analysis) was washed twice with water (2 ml each time). Concentrated (96%) sulfuric acid (8 ml) was added and the mixture was heated with stirring as it was described in Example 1. There was obtained 1.45 g of gaseous HFA. The yield of HFA was 58% of theory.

TABLE 1

| Solvent used (g) | Amt. of crude HFA obtained in −78° C. trap, g | Amt. of HFA gas after recondensation, g | Amt. of the residue* in the trap, g | HFA yield based on raw material, % | HFA yield based on the oxime conversion, % |
| --- | --- | --- | --- | --- | --- |
| CH₃CN (0.42) | 1.44 | 1.25 | 0.19 | 78 | 88 |
| Diglyme (1.34) | 1.38 | 1.16 | 0.21 | 73 | 82 |
| Pyridine (0.80) | 1.42 | 1.20 | 0.22 | 75 | 86 |
| Acetone (0.59) | 1.43 | 1.21 | 0.22 | 76 | - |
| DMAC** (0.89) | 1.59 | 1.29 | 0.19 | 81 | 91 |

*The residue was usually 60% HFA oxime and 30% HFA hydrate.
**DMAC is N,N-dimethyl acetamide.

EXAMPLE 4

HFA from hydrolysis of HFA oxime solvent complexes.

In this Example, a number of runs were carried out with different hexafluoroacetone oxime.solvent complexes. The same procedure was used as in Example 3 except, after completing the reaction (exothermic) of the HFA oxime with an equimolar quantity of solvent, an extra mole of solvent was added (without any heat evolution). The reaction mixture was washed twice with equal volumes of 15% hydrochloric acid solution and water and then refluxed with 10 ml

TABLE 2

| Solvent used (g) | Amt. of crude HFA obtained, g | Amt. of HFA gas recondensed, g | Amt. of the residue in the trap, g | HFA yield based on raw material, % | HFA yield based on the oxime conversion, % |
| --- | --- | --- | --- | --- | --- |
| CH₃CN (0.83) | 1.34 | 1.13 | 0.21 | 71 | 81 |
| Diglyme (2.70) | 1.31 | 1.10 | 0.21 (+0.06 HFA solid hydrate*) | 69 | 83 |
| CH₃COOH (1.21) | 1.08 | 0.79 | 0.29** (+0.1 solid HFA hydrate*) | 50 | 88 |

*This was deposited on the walls of the condenser.
**This comprises of 46% HFA hydrate (0.13 g) and 42% HFA oxime (0.12 g).

EXAMPLE 6

HFA from reaction of 1-methoxy-1perfluoroisobutene with sodium nitrite.

To 10.82 g (0.05M) of 1-methoxy-1perfluoroisobutene (of 94% purity) in 20 ml $CH_3CN$, 5.1 g (0.05M) of triethylamine was added while cooling and the mixture was left for 1 hour at room temperature to form the mesomeric hexafluoroisobutenolate methyl triethyl ammonium salt. Then 5.1 g (0.07M) of $NaNO_2$ was added and the resulting mixture was heated with vigorous stirring at 52–45° C. until carbon dioxide stopped evolving. The mixture was left standing overnight. Sodium fluoride and excess sodium nitrite were filtered off the mixture and 3.47 g of the salt mixture was obtained which contained 1.75 g of NaF ($NaNO_2$ was washed out by water). After washing the $CH_3CN$ solution with 10% sulfuric acid (two 25 ml washes), there was separated 16.0 g of organic material and 1.9 g was obtained from ether extraction of the combined water layers. The combined organic material was refluxed with 38 g of concentrated (96%) sulfuric acid to give 5.0 g of pure HFA after recondensation. The yield was 59% of theory (64% taking into account the starting ether purity).

EXAMPLE 7

HFA oxime from reaction of 1-methoxy-2H-octafluoroisobutane with nitrogen dioxide.

To 50.3 g (0.22M) of 1-methoxy-2H-octafluoroisobutane 42.8 g (0.42M) of triethylamine in 80 ml of acetone were added and the mixture was left stirring for 2 hours at a temperature not exceeding 40° C. Then $N_2O_4$ (22.6 g; 0.24M) was condensed slowly into the mixture at a temperature not higher than +7° C. and the reaction mixture was left overnight at room temperature. Short time (5 min.) heating to 65° C. was needed to accomplish the process (viz., the end of carbon dioxide evolution). The reaction mixture was washed 2 times with 10% solution of sulfuric acid (40 ml) and water (10 ml), and the organic layer (56.3 g) was separated. The water solution was extracted with methyl tert-butyl ether, the ether solution was dried, solvent was distilled out, and the residue (5.3 g) was added to the main organic layer. The combined organic material (61.6 g) was distilled in vacuum (approx. 20 mm Hg) into a trap (−78° C.) from a mixture it with 80 ml concentrated sulfuric acid. There was obtained 23.7 g of crude oxime (white solid at −78° C.) containing as determined by GC analysis 84.6% HFA oxime, 5% HFA, and some unknown impurities. The yield of the oxime is 51% of theory.

EXAMPLE 8

HFA or HFA oxime from the reaction of 1-methoxy-2H-octafluoroisobutane with nitrogen dioxide.

Following the same procedure used in Example 7, from 50 g (0.21M) of 1-methoxy-2H-octafluoroisobutane, 41.2 g (0.41M) of triethylamine, 23.2 g (0.25M) of $N_2O_4$ in 80 ml of acetone, there was obtained 56.0 g organic material and 4.95 g from ether extraction. The mixture of the two materials, 60.9 g, was divided into two portions. The 1st portion (38.6 g) and 40 ml of concentrated (96%) sulfuric acid was vacuum distilled (the temperature of the heating bath was not higher than 80° C.) and there was obtained 15.7 g of crude HFA oxime, which contained (as determined by GC) 86% of the oxime, 3% HFA, 2.5% of 2H-hexafluoroisobutyric acid, and 8% unknown contaminants. The yield of the oxime was 55% of theory. The 2nd portion (22.0 g) of the 60.9 g mixture and 40 ml of concentrated (96%) sulfuric acid was refluxed at 100–130° C. and there was obtained 8.3 g of crude HFA and 7.7 g of pure HFA after recondensation. The yield of HFA was 59% of theory.

EXAMPLE 9

HFA oxime from the reaction of 1-methoxy-2H-octafluoroisobutane with $N_2O_4$ and with solvent recovery.

The same procedure of Example 7 was used except that after the reaction with $N_2O_4$ ended, the acetone was distilled from the reaction mixture under vacuum into a trap (−78° C.), and it was not necessary to extract the water solution. Using 49.1 g of 1-methoxy-2H-octafluoroisobutane, 42.7 g of triethylamine, and 20.7 g of $N_2O_4$ in 80 ml acetone in the reaction, there was obtained 18.0 g of HFA oxime with purity (by GC analysis) of 94%. The yield was 44% of theory. And 64 ml (80%) of acetone was recovered.

Various modifications and alterations of this invention will become apparent to those skilled in the art without departing from the scope and spirit of this invention.

What is claimed is:

1. A process for the production of hexafluoroacetone, which comprises heating hexafluoroacetone oxime, or hexafluoroacetone oxime complexed with an organic solvent wherein the organic solvent is selected from the group comprising nitriles, tertiary amines, dialkylamides, ketones, simple ethers, alcohols, and esters, and organic acids containing from 1 to 4 nonhalogenated aliphatic carbon atoms the skeletal chain of which may contain one or more catenary heteroatoms, with concentrated mineral acid to hydrolyze the oxime, and recovering the resulting hexafluoroacetone.

2. The process of claim 1 wherein said heating is carried out by refluxing said oxime or complex thereof with said mineral acid.

3. The process according to claim 1 wherein said hexafluoroacetone oxime is in the form of its acetonitrile complex.

4. The process of claim 1 wherein said hexafluoroacetone oxime is in the form of its acetone complex.

5. The process of claim 1 wherein said mineral acid is concentrated sulfuric acid.

6. A process for the production of hexafluoroacetone, which comprises:
   a. reacting a trialkyl amine wherein each constituent group contains from 1 to 3 straight chained carbon atoms with the alcohol adduct of perfluoroisobutene;
   b. reacting the resulting salt product in a solvent with (i) an alkali or alkaline earth metal nitrite or (ii) with dinitrogen tri- or tetra-oxide to produce a hexafluoro oxime solvent complex product; and
   c. hydrolyzing the latter product with concentrated mineral acid to produce hexafluroacetone;

wherein said process is carried out without isolation or recovery of the products of steps a and b.

7. The process according to claim 6 wherein said alcohol is methanol, said trialkyl amine is triethylamine, said nitrite is sodium nitrite, said dinitrogen tri- or tetra-oxide is dinitrogen tetroxide, and said mineral acid is concentrated sulfuric acid.

8. The process according to claim 6 wherein said salt product is reacted with dinitrogen tetroxide.

9. The process of claim 6 wherein said alcohol is methanol.

10. The process of claim 6 wherein said trialkyl amine is triethylamine.

11. The process of claim 6 wherein said alkali or alkaline earth metal nitrite is sodium nitrite.

12. A process for the production of hexafluoroacetone oxime, which process comprises reacting an alkanol adduct of perfluoroisobutene with a tertiary amine, reacting the resulting mesomeric hexafluoroisobutenolate tetra-alkylammonium salt in a solvent with (i) an alkali or alkaline earth metal nitrite or (ii) dinitrogen tetra- or tri-oxide, washing the resulting ammonium salts and the solvent from the resulting reaction product mixture, treating the washed product with concentrated mineral acid, and distilling hexafluoroacetone oxime from the resulting acid mixture.

13. The process according to claim 12 wherein said alkanol is methanol, said tertiary amine is triethylamine, said nitrite is sodium nitrite, said dinitrogen tri- or tetra-oxide is dinitrogen tetroxide, and said mineral acid is sulfuric acid.

14. The process according to claim 12 wherein said steps of reacting said adduct with said tertiary amine, and said step of reacting said ammonium salt with said nitrite or with said dinitrogen tri- or tetra-oxide are all carried out in sequence without isolation or recovery of the resulting intermediate products.

15. A process for the production of hexafluoroacetone oxime, which comprises reacting mesomeric perfluoroisobutenolate quaternary methyl triethyl ammonium salt with sodium nitrite in acetonitrile or dinitrogen tetroxide in acetone, washing the resulting reaction product, treating the washed product with concentrated sulfuric acid, and distilling hexafluoroacetone oxime from the resulting acid mixture.

16. The process of claim 6 wherein said alcohol is a lower alkanol.

* * * * *

UNITED STATES PATENT AND TRADEMARK OFFICE
CERTIFICATE OF CORRECTION

PATENT NO. : 5,466,879
DATED : November 14, 1995
INVENTOR(S) : Yuri Cheburkov

It is certified that error appears in the above-indentified patent and that said Letters Patent is hereby corrected as shown below:

TITLE PAGE:
Other Publications

Third Reference, delete "Hexafluoroactetone" and insert therefore --Hexafluoroacetone--.

Fourth Reference, delete "181" and insert therefore --190-192--.

Col. 1, line 44, delete "NOH.Solvent" and insert therefore --NOH·Solvent--.

Col. 2, line 35, delete "acetates." and insert therefore --acetate--.

Col. 3, line 5, delete "(CF$_3$)2CHCOF" and insert therefore --(CF$_3$)$_2$CHCOF--.

Col. 3, line 17, delete "khim." and insert therefore --Khim.--.

Col. 3, line 23, after "preparation" insert therefore --of--.

Col. 3, lines 31-34, the equation should read as follows:

Col. 3, lines 50-55, the equation should read as follows:

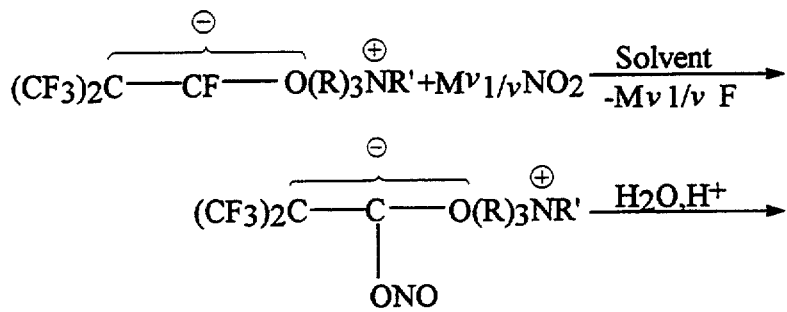

UNITED STATES PATENT AND TRADEMARK OFFICE
CERTIFICATE OF CORRECTION

PATENT NO. : 5,466,879
DATED : November 14, 1995
INVENTOR(S) : Yuri Cheburkov

It is certified that error appears in the above-indentified patent and that said Letters Patent is hereby corrected as shown below:

Col. 3, lines 58-60, the equation should read as follows:

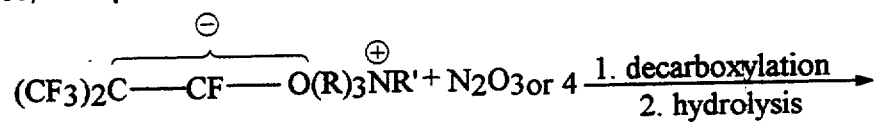

Col. 4, lines 5-9, the equation should read as follows:

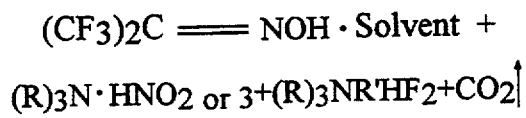

Col. 5, line 14, delete "oxime.solvent" and insert therefore --oxime·solvent--.

Col. 5, line 44, delete "oxime.solvent" and insert therefore --oxime·solvent--.

Co. 7, line 4, delete "1perfluoroisobutene" and insert therefore --1-perfluoroisobutene--.

Col. 7, line 44, after "from a mixture" delete "it with" and insert therefore --of--.

Signed and Sealed this

First Day of October, 1996

Attest:

BRUCE LEHMAN

Attesting Officer

Commissioner of Patents and Trademarks